(12) United States Patent
Farrar et al.

(10) Patent No.: US 7,495,036 B2
(45) Date of Patent: Feb. 24, 2009

(54) POLYMERIC COMPOSITIONS AND THEIR PRODUCTION AND USES

(76) Inventors: David Farrar, Eye Dale Court, Ashton Walk, Idle, Bradford BD10 8RN (GB); Jason Lloyd Mellor, 25 The Lodge, Linthwaite, Huddersfield HD7 5TG (GB); Adrian Swinburne Allen, Rosebank, 50 Raikes Road, Skipton, North Yorkshire BD23 1LS (GB); Frederick Anthony Bell, 9 Rossett Drive, Harrogate, North Yorkshire HG2 9NS (GB)

( * ) Notice: Subject to any disclaimer, the term of this patent is extended or adjusted under 35 U.S.C. 154(b) by 441 days.

(21) Appl. No.: 10/523,016

(22) PCT Filed: Jul. 31, 2003

(86) PCT No.: PCT/GB03/03347

§ 371 (c)(1),
(2), (4) Date: Nov. 3, 2005

(87) PCT Pub. No.: WO2004/013209

PCT Pub. Date: Feb. 12, 2004

(65) Prior Publication Data

US 2006/0111476 A1 May 25, 2006

(30) Foreign Application Priority Data

Aug. 2, 2002 (GB) ................ 02255426.5

(51) Int. Cl.
*A61K 8/72* (2006.01)
*C08K 5/05* (2006.01)
*B03D 1/016* (2006.01)

(52) U.S. Cl. ........................ 523/105; 523/223; 524/379; 524/551; 524/556

(58) Field of Classification Search ............... 523/105, 523/223; 524/379, 551, 556
See application file for complete search history.

(56) References Cited

U.S. PATENT DOCUMENTS

| 4,778,836 | A | * | 10/1988 | Farrar et al. ............... 524/35 |
| 4,806,345 | A | | 2/1989 | Bhattacharyya |
| 5,171,781 | A | | 12/1992 | Farrar et al. |
| 5,603,926 | A | | 2/1997 | Matsumoto et al. |
| 6,833,406 | B1 | * | 12/2004 | Green et al. ............. 524/588 |

FOREIGN PATENT DOCUMENTS

| EP | 0202780 | 4/1986 |
| EP | 0824914 A1 | 8/1997 |
| EP | 0872491 A1 | 4/1998 |
| WO | WO97/34945 | 3/1997 |
| WO | WO00/01757 | 6/1999 |
| WO | WO02/057322 | 1/2002 |

* cited by examiner

*Primary Examiner*—Kriellion A Sanders

(57) ABSTRACT

A clear personal care or other aqueous gel is formed from dry polymer particles which are free of materials which render the gel cloudy and which are made by reverse phase emulsion polymerisation. The polymerisation process involves distilling water from the emulsion in the presence of sufficient non-aqueous liquid to prevent breakage of the emulsion and then washing the polymer particles with isopropanol or other suitable solvent and evaporating the solvent.

13 Claims, No Drawings

POLYMERIC COMPOSITIONS AND THEIR PRODUCTION AND USES

This invention relates to powdered polymer having very small primary particle size and which is soluble or swellable in water to form a homogeneous, clear, gel, and to the production of this polymer.

It is conventional practice to thicken an aqueous composition by adding water-soluble or water-swellable thickening polymer to the composition. It is often desirable to provide this polymer in powder form, namely as a dry product in the form of particles, which may be individual primary particles or which may be aggregates of such particles and which disintegrate when mixed into water.

Powdered water-soluble or water-swellable polymer particles can be made by various polymerisation processes including bulk polymerisation followed by comminution, solution polymerisation followed by drying (for instance by spray drying), precipitation polymerisation followed by recovery of the precipitate and drying, reverse phase bead polymerisation followed by recovery of dry beads and comminution if small primary particles are required, and emulsion polymerisation followed by recovery of the polymer from the emulsion. Examples of bulk and bead polymerisations to give coarse (preferably all above 150 µm) superabsorbent powders are in EP-A-872491, but these cannot give a clear homogeneous gel because the coarse beads retain individual integrity.

Each method gives a powdered product having different physical form (such as shape and size) and also having different types and degrees of contamination. Precipitation polymerisation and reverse phase emulsion polymerisation is generally preferred when a very small primary particle size (all below 20 µm) is required.

The selection of the polymerisation method and the monomers to be polymerised also influences the molecular weight (including the molecular weight distribution) which is conveniently achieved by the polymerisation. For instance some anionic polymers can conveniently be made by methods such as precipitation polymerisation to give polymers having good molecular weight properties and low contamination, but such techniques tend to be less satisfactory for cationic monomers. In order to obtain the optimum molecular weight properties using cationic monomers it is generally preferred to use reverse phase emulsion polymerisation, but this tends to result in emulsions, or powdered products, which are contaminated with materials that reduce the clarity of the final gel.

Clarity of the gel is particularly desirable in personal care compositions such as cosmetic compositions and topical pharmaceutical compositions. The thickening polymer in these frequently is a cationic polymer, for instance as described in U.S. Pat. No. 4,806,345 and U.S. Pat. No. 5,603,926. The problem of clarity is mentioned in EP-A-824914. This disclosure describes cationic thickeners which are in the form of stable emulsions, but we are concerned with the problem of providing a thickener in the form of a finely divided powder.

It would therefore be desirable to produce an improved way of making a very finely divided powdered polymer which can give a gel having good clarity, and in particular it would be desirable to provide this where the polymer is a cationic polymer.

According to one aspect of the invention, we make a dry powder formed of primary particles, or aggregates of primary particles, of a water-soluble or water-swellable polymer wherein the powder dissolves or swells in water to form a gel, by a method which comprises forming an emulsion of aqueous monomer in non-aqueous liquid, optionally in the presence of an emulsifier, initiating polymerisation and allowing polymerisation to complete, distilling water from the emulsion until the emulsion is substantially dry, the distillation being conducted while maintaining a sufficient amount of the non-aqueous liquid to prevent breakage of the emulsion, separating the non aqueous liquid from the polymer particles by a process comprising washing the substantially dry emulsion, or a slurry or cake of dry polymer particles separated from it, with an organic, volatile, solvent which is a solvent for non-aqueous liquid and for the emulsifier (if used) and which does not dissolve or swell the polymer particles and which is substantially miscible with water, separating the washed polymer particles as a cake or slurry of the particles wetted by the solvent, and evaporating the solvent from the cake or slurry and thereby providing the dry powder.

The polymer is made by reverse phase emulsion polymerisation of water soluble or water swellable ethylenically unsaturated monomer or monomer blend. Any of the conventional cationic, non-ionic and anionic ethylenically unsaturated monomers can be used, together with blends of the monomers.

The polymer is preferably cationic. The method is particularly advantageous for making cationic powdered thickeners, and especially for providing such thickeners which give a clear gel. Accordingly the monomer or monomer blend which is polymerised preferably contains one or more cationic ethylenically unsaturated monomers, or a blend of such monomer with non-ionic monomer and/or anionic monomer. The amount of cationic monomer is preferably such that the monomer is predominantly cationic.

According to another aspect of the invention, we provide a powder formed of primary particles, or aggregates of primary particles, of a water-soluble or water-swellable polymer wherein the product dissolves or swells in water at a gelling pH to form a gel, and wherein the primary particles preferably have a size below 20 cm and have the characteristic, substantially spherical, structure of polymer particles made by reverse phase emulsion polymerisation, and the composition gives a 0.5% gel in water, wherein the gel has a clarity of at least 90% at 430 nm (as explained below). The clarity is preferably at least 93% or 95%, and most preferably it is at least 97 or 98%.

Whether or not the polymer particles have the characteristic, substantially spherical, structure including shape of particles made by reverse phase emulsion polymerisation can easily be determined by microscopic examination. Particles made by spray drying may be substantially spherical but they can be seen by microscopic examination to be very porous and shell like and so the product includes pieces of fractured shell. Particles made by solution, bulk or precipitation polymerisation all have characteristic, non-spherical, shapes. Particles made by reverse phase emulsion polymerisation have a dry size typically in the range 0.5 to 20 µm, often 1 to 10 µm, and when examined by a microscope are predominantly solid spheres. For instance at least 80% (by weight) of the particles in any particular microscopic image typically are truly spherical or substantially spherical, although there can be minor amounts of broken, pear-shaped or other deformed solid particles. Accordingly, the primary particles of the invention have these typical characteristics. The mean particle size is generally in the range 0.5-10 µm. The mean size is usually at least 1 µm. It is usually below 5 µm and so may be, for instance, 1-2 µm. Generally substantially all the particles (e.g., at least 95% by weight) are below 20 µm and preferably below 10 µm Normal ways of conducting reverse phase emulsion polymerisation of a monomer result in the particles being contaminated by significant amounts of cloud-forming impurities which were included as essential components in the reverse phase emulsion polymerisation process. For instance it is normal to use a significant amount of emulsifier in order to stabilize the emulsion initially and it is normal to select a non-aqueous liquid as the continuous phase, and optionally also a polymeric stabilizer, to improve the stability of the emulsion, especially during subsequent evaporation of water from it, and parts of these remain on the particles.

The powdered products of the invention are preferably free of cloud-forming amounts of polymeric stabilizer, hydrocarbon and emulsifier.

As a result of using reverse phase emulsion polymerisation for making the polymer particles, it is easily possible to optimize the eventual viscosifying properties because reverse phase emulsion polymerisation allows this to be done, in accordance with common general knowledge, much more easily than is achievable when using other types of polymerisation, especially when the polymer is cationic.

Preferred cationic monomers are cationic esters of acrylic of methacrylic acid, preferably a cationic methacrylate. Accordingly, the polymer is generally a polymer of 50 to 100 mole percent water soluble cationic ester of methacrylic acid and 0 to 50 mole percent of other water soluble ethylenically unsaturated monomers. If comonomer is present, it may be non-ionic (for instance acrylamide) or in some instances a minor amount of anionic comonomer can be present.

The preferred cationic monomer is an acid addition or quaternary ammonium salt of a dialkylaminoethyl methacrylate, and is most preferably the methyl chloride quaternary salt of dimethylaminoethyl methacrylate.

The polymer can be linear but is usually lightly cross linked and so it is normally formed in the presence of a cross linking agent. As is conventional, this cross linking agent can be a polyethylenically unsaturated material. The amount of cross linking agent is usually low in order that the powder particles swell and dissolve in water to form a clear, homogeneous gel instead of remaining as discrete, or partly discrete, swollen particles. Generally the cross linking agent is a polyethylenically unsaturated material in an amount of below 200 ppm, often below 130 ppm, e.g., 50-100 ppm, by weight of monomer.

The preferred polymers are homopolymers of the cationic ester of methacrylic acid, copolymerized with, usually, 0.001 to 0.1 mole percent (preferably below 130 ppm by weight) of a polyethylenically unsaturated cross linking agent.

Suitable cross linking agents are methylene bis acrylamide or any of the conventional covalent cross linking agents used for making swellable viscosifying polymers.

The non-aqueous liquid is preferably volatile and preferably is a hydrocarbon. Preferred hydrocarbons are aliphatic hydrocarbons, preferably branched or linear isoparaffins. They preferably have a boiling point at normal pressure of below 200° C., most preferably in the range 150 to 180° C. The boiling point under normal pressure is preferably above 90° C. and most preferably is above 100 or 120° C. This allows for the polymerisation exotherm to run at optimum temperatures for polymer quality without volatilization of the non-aqueous liquid. Examples of suitable non-aqueous liquids are the materials sold under the trade names Isopar G and Multipar G.

Preferably the continuous phase of the emulsion consists substantially only of the hydrocarbon or other non-aqueous liquid. The continuous phase preferably is wholly or substantially free of non-volatile non-aqueous liquid and/or polymeric stabilizer (both of which are conventional in prior processes).

It is usually desirable to include some emulsifier in order to facilitate formation and stability of the emulsion but in the invention the amount of stabilizer preferably is minimized by conducting the polymerisation on a more dilute solution of monomer than is conventional in reverse phase polymerisation for making the relevant polymers. Thus conventional processes usually have a monomer concentration of above about 72% (monomer based on monomer plus water) and with the total amount of water in the emulsion, based on the total weight of the emulsion, often being around 15%. In the invention, however, we prefer to use more water in the emulsion so that the aqueous monomer solution is more dilute.

Typically the concentration of monomer is below 70% and is usually in the range 50 to 68% (based on monomer plus water). The amount of water, based on the total weight of the emulsion, is now usually in the range 20 to 40%, preferably 22 to 30%. Typically the amount of polymer is 35 to 55%, often around 40 or 45% to 50%, and the amount of the volatile non-aqueous liquid is generally 20 to 40%, often around 25 to 35%.

With such amounts, and with routine selection of the volatile hydrocarbon or other non-aqueous liquid, it is possible to minimize, and sometimes even to eliminate, the emulsifier while maintaining emulsion stability. If emulsifier is being used then it can be any of the conventional emulsifiers for water-in-oil polymerisation, typically emulsifiers having HLB of 3.5 to 6. A preferred material is the material commercially available under the trade mark Span 80. Other suitable emulsifiers include glyceryl mono-oleate and sorbitan sesqui-oleate.

The amount of emulsifier is usually from 0.1 or 0.5 to 1, 1.5 or 2% based on the weight of emulsion or 0.2 to 2, 3 or sometimes 4% based on the weight of monomer.

The emulsion may be formed in conventional manner by homogenization of the oil and aqueous phases to provide an emulsion having a particle size (for the aqueous particles) which will provide the desired primary polymer particle size after polymerisation and drying.

Polymerisation may be achieved by purging the emulsion with nitrogen gas and adding initiator. This addition is usually made throughout most or all of the period of the polymerisation reaction. In order to facilitate rapid distribution of the initiator throughout the emulsion, some or all of the initiator is preferably added as an emulsion or solution in non-aqueous liquid. Thermal initiator can be used as part or all of the initiator system but it is often adequate to rely on a redox system, for instance with sodium metabisulphite being added as an emulsion in non-aqueous liquid and t-butyl hydroperoxide or other redox couple being added as a solution in non-aqueous liquid. The rate of addition and the duration of addition is conducted in conventional manner and the progress of the polymerisation is monitored in conventional manner.

When it is judged that the polymerisation has gone to completion, the emulsion is dried by distillation of the aqueous phase from it. Distillation is normally conducted under reduced pressure with reflux of the non-aqueous liquid while the water is removed.

It is necessary to ensure that the emulsion does not break during this process, i.e., it must not break to an extent sufficient to cause serious congealing of the polymer particles. It is often desirable to add an additional amount of the non-aqueous liquid prior to or during this distillation stage so as to reduce the risk of breakage of the emulsion by maintaining the liquid content of the emulsion substantially constant. For instance the amount of additional non-aqueous liquid which is added may be 0.2 to 1.5 times, often around 0.5 to 1 times, the amount of water which is being removed.

The distillation is conducted until the water removal has dropped to a very low rate, preferably near zero. This occurs when the emulsion is substantially dry, for instance having a water content (based on the weight of polymer) of below 10% and usually below 5% by weight.

The dry polymer particles (and aggregates of these) are then separated from the non-aqueous liquid by a process comprising washing the substantially dry polymer particles with an appropriate volatile solvent. The solvent may be added to the entire mixture of non-aqueous liquid and polymer particles (so that the entire emulsion is washed) or some of the non-aqueous liquid may be separated, for instance by filtration or centrifugation, before the washing to form a slurry or cake, and it may be this slurry or cake which is washed.

The amount of the solvent is often such that the percentage of polymer, based on polymer and solvent, is 1 to 50%, often 1 to 15%, preferably 2 to 10%.

After the washing, the polymer particles are separated from the solvent, again usually by a filtration or centrifugation or other physical separation step, to form a cake or slurry. The particles can be washed again with more solvent if required. Preferably the content of polymer in the final cake or slurry of particles and solvent is at least 30%, preferably at least 45%, and most preferably at least 50, 55 or 60%, up to 70% or more.

Residual solvent is then evaporated from the resultant cake or slurry of polymer particles, for instance by oven or other warm air drying so as to provide the desired dry powder. This may be formed mainly of individual primary particles but it is generally desirable that many or substantially all of the primary particles are present as aggregates since this reduces handling problems and increases the bulk density. The aggregates should be readily disintegratable upon stirring into the medium which is to be thickened so as to release the primary particles into the medium.

In general, clarity improves as the amount of solvent used for the washing is increased and as the amount of solvent which has to be evaporated is reduced.

The solvent which is used for the washing must be a solvent for the non-aqueous liquid of the continuous phase of the emulsion in order that the solvent washes that liquid away from the particles. If emulsifier was used, it must also be a solvent for the emulsifier, so as to wash that away from the particles. Whether or not any particular solvent is a good solvent for any particular emulsifier can be checked by a simple routine test. The solvent must not dissolve, soften or swell the polymer particles to such an extent as to detract from the powder properties of the final product and preferably the solvent does not cause any dissolution or swelling of the particles.

The solvent must be sufficiently volatile that it can be conveniently evaporated by warm air or other suitable drying technique. Preferably the solvent is sufficiently volatile that there is no risk of any traces of solvent remaining on the particles after drying. However, it is, in any event, desirable that the solvent is substantially fully miscible with water so that any traces of solvent on the particles will not cause cloudiness of the final gel.

The solvent is usually a polar solvent. Preferably it is a C1-4 alcohol or ketone. Although methanol has been proposed previously for washing large superabsorbent anionic polymer particles in EP 872941, methanol and ethanol may tend to cause too much softening or swelling of the very small particles of polymers in the invention (especially the cationic polymers) with the result that the primary particles may tend to fuse into coarse granules which do not disintegrate easily into the primary particles. Acetone has also been proposed but tends to be an inadequate solvent for some grades of Span 80 or other emulsifier. Accordingly preliminary testing will often show that methanol, ethanol and acetone are not entirely satisfactory with some or most powdered polymers in the invention. The preferred solvent is generally isopropyl alcohol.

In some instance it is desirable to include with the solvent a small amount of a water-miscible cosolvent for any emulsifier. Suitable cosolvents are emulsifiers having a long ethoxy chain whereby the hydrophilic component promotes dissolution of the emulsifier into the volatile solvent. An example is ethoxylated sorbitan monolaurate, typically having more than ten ethoxy groups, preferably twenty ethoxy groups. The addition of a cosolvent in this manner can help to provide final "polishing" of the clarity of the gel. Alternatively the cosolvent emulsifier may be incorporated into the gel formed from the dry product.

The dry product, consisting of the primary particles or aggregates of primary particles, can then be incorporated into a personal care or other composition as a viscosifier in conventional manner. The composition should be formulated to have a pH at which the polymer gels to form a gel of the dissolved or swollen polymer particles, i.e., the gelling pH. For cationic polymers, the gelling pH can be as low as 2.5. Although the composition often has pH below 7, for instance 4.5 to 6.8, stable gels of cationic polymers can be formed in the invention having pH values higher than this, for instance up to 9 or even 10 or 10.5, when using cationic polymers in accordance with the invention. Naturally the optimum pH depends on the monomers which are used and on the other components of the composition.

As a result of providing a powdered composition formed of particles of water-soluble or water-swellable polymer free of cloud-forming amounts of polymeric stabilizer, hydrocarbon or other non-aqueous liquid, and emulsifier, despite having been made by reverse phase polymerisation, the powdered composition gives a clear gel in water. In particular, the process of the invention can easily be conducted so that the composition gives a gel which has a clarity of at least 85% and preferably at least 90%, and most preferably at least 93% or, especially, at least 95%.

In this specification, all clarity values are determined at 430 nm, since this gives maximum resolution. The protocol is designed for determining the clarity of a gel formed by dissolving cationic polymer in deionizer water, without any deliberate pH adjustment. If the relevant polymer does not dissolve or swell to an optimum extent when dissolved merely in water, then some pH adjustment may be applied. A suitable protocol is described in the Noveon Standard Test Procedure 485-D September 1993. A more detailed protocol is as follows:—

1. The clarity measurement is performed on a 0.5% solution of polymer in deionizer water, using a Colorimeter such as a Brinkmann Probe Colorimeter Model PC 801.

2. The polymer is dried at 80° C. for 1 hour.

3. The polymer is allowed to cool and 1.0000 g+/−0.002 weighed accurately on an analytical balance into a weigh boat.

4. 199 g+/−0.02 g deionizer water is weighed into a 250 ml plastic beaker.

5. The beaker is clamped in place and stirred using a 50 mm radial flow impeller, placed near the bottom of the beaker.

6. The polymer is added slowly to the deionizer water to avoid clumping since the presence of agglomerated particles is would interfere.

7. After the solution starts to thicken the stirrer speed is increased to 2000 rpm for 5 minutes to ensure full hydration.

8. Using a spatula, a portion of the solution is transferred to a 50 mL centrifuge tube.

9. The tube is placed in the centrifuge and spun for five minutes at the maximum speed setting. Centrifugation is for elimination of air bubbles since these would interfere.

10. The calorimeter is turned to % T and a 430 nm filter is provided, and a five minute warm-up period is allowed.

11. A 1 cm cuvette is filled with deionizer water and the 100% T Coarse Control Knob is adjusted until the reading indicates 100.0% or very close. The Fine Control is used to obtain an exact reading of 100.0%.

12. Using a spatula, a portion of the solution is transferred to a 2 cm cuvette avoiding air entrapment.

13. The % Transmission (or Clarity) is read directly from the instrument.

The following is an example of the invention.

An emulsion was formed of 6673 g of a 75% aqueous solution of the MeCl quaternary salt of dimethylaminoethyl methacrylate, 12.8 g citric acid, 1043 g deionizer water, 11.4 g Tetralon B and 0.693 g methylene bis acrylamide in 3227 g Multipar G containing 80.6 g Span 80 as emulsifier. The emulsion was made by forming the aqueous phase and the oil phase separately and then homogenizing the oil phase into the aqueous phase for 20 minutes using a Silver son with cooling to keep the temperature at or below 20° C. The emulsion was then transferred to a conventional polymerisation pot, degassed for 30 minutes and held under nitrogen. A 0.5% emulsion of SMBS in Isopar G and a 0.5% solution of TBHP in Isopar G were fed into the emulsion at 100 ppm per hour, and the temperature was monitored every 60 seconds to ensure that the polymerisation was continuing satisfactorily.

After the completion of the full exotherm was observed, the initiator feeds were continued for a further 20 minutes. They were then terminated, and the reaction mixture was left stirring for a further 20 minutes to allow polymerisation to complete.

200 g of the product was removed from the vessel and was diluted with 50 g Isopar and was then subjected to distillation using a rotary evaporator under full vacuum at a temperature ranging between 25 and 80° C. until the final product was a dry emulsion of the dry polymer particles in hydrocarbon.

Isopropyl alcohol in an amount of 95% based on the weight of polymer and isopropyl alcohol was then mixed with the product so as to wash the polymer particles. The resultant mixture was then separated by decantation and centrifugation and the resultant cake had a polymer content of 61%. The residual solvent was evaporated from the cake in an oven at less than 60° C. until a dry weight (1 gm for 1 hour at 110° C.) of at least 90% is achieved (for instance at 40° C. for 2 days).

The resultant powder consisted of substantially spherical solid primary particles and easily disintegratable aggregates of these. The powder was easily distributed into water to give a clear gel having a clarity of 98% at 430 nm.

In other tests, a clarity of 99% was obtained when the amount of isopropyl alcohol was 98.75% and the resultant cake or slurry was concentrated to 58% polymer before the drying, but a clarity of only 75% was obtained when the amount of isopropyl alcohol was 95% but the resultant cake or slurry only contained 46.5% polymer prior to the final evaporation of solvent in the oven. In another example a clarity of 95% was achieved when the amount of isopropyl alcohol was 97.5% and the slurry or cake, before final evaporation in the oven, had a polymer content of 42.3%.

In another process where the clarity, when using isopropyl alcohol alone, was 88%, a clarity value of above 95% was achieved by including with the solvent 1% of 20 mole ethoxylate of sorbitan monolaurate.

The invention claimed is:

1. A process of making a dry powder formed of primary particles, or aggregates of primary particles, or a polymer wherein the primary particles have a size below 20 µm and the powder can dissolve or swell in water to form a clear gel, the process comprising forming an emulsion of aqueous ethylenically unsaturated cationic monomer in non-aqueous liquid optionally in the presence of an emulsifier, initiating polymerisation and allowing polymerisation to complete, distilling water from the emulsion until the emulsion is substantially dry, the distillation being conducted while maintaining a sufficient amount of non-aqueous liquid in the emulsion to prevent breakage of the emulsion, separating the non-aqueous liquid from the polymer particles by a process comprising washing the substantially dry emulsion, or a slurry or cake of dry polymer particles separated from it, with a volatile organic solvent which is a solvent for the non-aqueous liquid and for the emulsifier (if used) and which does not dissolve or swell the polymer particles and which is substantially miscible with water, separating the washed polymer particles as a cake or slurry of the polymer particles wetted by the solvent, and evaporating the solvent from the cake or slurry and thereby providing the dry powder, wherein the powder is swellable in water to form a gel with optical clarity.

2. A process according to claim 1 in which the polymer is a cationic polymer.

3. A process according to claim 1 in which volatile non-aqueous liquid is added to the emulsion after the polymerisation and before or during the distillation of water from the emulsion.

4. A process according to claim 1, in which the amount of the volatile solvent utilised for washing the substantially dry emulsion or the polymer particles separated from the dry emulsion is from 85 to 99% based on the weight of solvent and polymer.

5. A process according to claim 1, in which the amount of the volatile solvent in the slurry or cake which is subjected to the evaporation is at least 50% by weight based on the weight of solvent and polymer.

6. A process according to claim 1, in which the volatile solvent is isopropyl alcohol.

7. A process according to claim 1, in which the concentration of monomer in the emulsion is below 70% by weight based on the weight of monomer and water and the emulsion contains 35 to 55% by weight of the monomer, 20 to 45% by weight of the non-aqueous liquid and 20 to 40% by weight of the water, all based on the weight of monomer, volatile non-aqueous liquid and water.

8. A powder formed of particles, or aggregates of particles, of a cationic polymer wherein the product can dissolve or swell in water to form a gel, characterised in that the particles have a size below 20 μm and have the characteristic, substantially spherical, shape of polymer particles made by reverse phase emulsion polymerisation, and the composition gives a 0.5% gel in water at a gelling pH wherein the gel clarity is at least 90% at 430 nm.

9. A product according to claim 8 in which the cationic polymer is a cationic polymer of 50 to 100 mole percent of a water soluble cationic ester of methacrylic acid, 0 to 50 mole percent other water soluble ethylenically unsaturated monomer, and optionally cross linking agent, and in which the polymer is preferably a cross linked homopolymer of the methyl chloride quaternary salt of dimethylaminoethyl methacrylate.

10. A personal care composition thickened by a composition made by a process according to claim 1.

11. A personal care composition thickened by a product according to claim 8.

12. A process according to claim 1, in which the amount of the volatile solvent utilised for washing the substantially dry emulsion or the polymer particles separated from the dry emulsion is from 90 to 98% based on the weight of solvent and polymer.

13. A process according to claim 1 in which the cationic polymer is a cationic polymer of 50 to 100 mole percent of a water soluble cationic ester of methacrylic acid, 0 to 50 mole percent other water soluble ethylenically unsaturated monomer, and optionally cross linking agent, and in which the polymer is preferably a cross linked homopolymer of the methyl chloride quaternary salt of dimethylaminoethyl methacrylate.

* * * * *